United States Patent
Chang et al.

(10) Patent No.: US 12,031,976 B2
(45) Date of Patent: Jul. 9, 2024

(54) SCREENING METHOD FOR THERAPEUTIC SUBSTANCE FOR PREVENTING OR TREATING BRONCHOPULMONARY DYSPLASIA (BPD)

(71) Applicant: SAMSUNG LIFE PUBLIC WELFARE FOUNDATION, Seoul (KR)

(72) Inventors: Yun Sil Chang, Seoul (KR); Won Soon Park, Seoul (KR); Dong Kyung Sung, Seoul (KR); Young Eun Kim, Gyeonggi-do (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 918 days.

(21) Appl. No.: 17/050,148

(22) PCT Filed: May 3, 2019

(86) PCT No.: PCT/KR2019/005365
§ 371 (c)(1),
(2) Date: Jan. 22, 2021

(87) PCT Pub. No.: WO2019/212305
PCT Pub. Date: Nov. 7, 2019

(65) Prior Publication Data
US 2023/0028447 A1    Jan. 26, 2023

(30) Foreign Application Priority Data

May 4, 2018   (KR) ........................ 10-2018-0051692
May 3, 2019   (KR) ........................ 10-2019-0052188

(51) Int. Cl.
*C07H 21/02*   (2006.01)
*G01N 33/50*   (2006.01)

(52) U.S. Cl.
CPC ..... *G01N 33/5023* (2013.01); *G01N 33/5082* (2013.01)

(58) Field of Classification Search
CPC .......................... G01N 33/5023; C12N 15/113
See application file for complete search history.

(56) References Cited

FOREIGN PATENT DOCUMENTS

KR    10-2012-0082271 A    7/2012
KR    10-2014-0024310 A    2/2014
WO    WO-03-074069 A2     9/2003

OTHER PUBLICATIONS

Coalson et al. (Seminars in Perinatology, 30, 4, 2006, 179-184).*
Committee on Fetus and Newborn, Pediatrics, 109:330-8, 2002.
Chang et al., "Human Umbilical Cord Blood-Derived Mesenchymal Stem Cells Attenuate Hyperoxia-Induced Lung Injury in Neonatal Rats", Cell Transplantation, vol. 18, pp. 869-886, 2009.
Chang et al., "Intratracheal Transplantation of Human Umbilical Cord Blood-Derived Mesenchymal Stem Cells Dose-Dependently Attenuates Hyperoxia-Induced Lung Injury in Neonatal Rats", Cell Transplantation, vol. 20, pp. 1843-1854, 2011.
Chang et al., "Timing of Umbilical Cord Blood Derived Mesenchymal Stem Cells Transplantation Determines Therapeutic Efficacy in the Neonatal Hyperoxic Lung Injury", PloS One, 2013, p. 1-11.
Ballabh, P. et al., Respiratory Burst Activity in Bronchopulmonary Dysplasia and Changes With Dexamethasone,, Pediatric Pulmonology 35:392-399 (2003).
Li, S. Q. et al., The expression of formyl peptide receptor 1 is correlated with Tumor Invasion of Human Colorectal Cancer, Scientific Reports, 7: 5918, pp. 1-26.
International Search Report from corresponding PCT Application No. PCT/KR2019/005365, dated Aug. 27, 2019.

* cited by examiner

*Primary Examiner* — Amy Rose Hudson
(74) *Attorney, Agent, or Firm* — Harness, Dickey & Pierce, P.L.C.

(57) ABSTRACT

The present invention relates to a screening method for a therapeutic agent for pulmonary damage induced by the administration of high-concentration oxygen, and more specifically, to a screening method for a candidate material for a therapeutic agent for bronchopulmonary dysplasia (BPD) induced by the administration of high-concentration oxygen. The present inventors have discovered that FPR1 is over-expressed in lung tissues exposed to high-concentration oxygen, and as a result of focusing on the correlation between the expression of FPR1 and the development of BPD, have confirmed that BPD can be suppressed by inhibiting the expression or activity of FPR1. In view of this fact, a prophylactic or therapeutic material for BPD may be discovered in a rapid and accurate manner by checking whether the expression or activity level of FPR1 is inhibited, and thus, the screening method of the present invention may be beneficially used to effectively select and develop therapeutic agents for BPD.

3 Claims, 9 Drawing Sheets

Specification includes a Sequence Listing.

SEQUENCE LISTING

```
<160> NUMBER OF SEQ ID NOS: 10

<210> SEQ ID NO 1
<211> LENGTH: 1371
<212> TYPE: DNA
<213> ORGANISM: Homo sapiens

<400> SEQUENCE: 1
aatcattaga  gcctgagtca  ctctccccag  gagacccaga  cctagaacta  cccagagcaa      60
gaccacagct  ggtgaacagt  ccagcctgtc  tccagttgga  ctagccacaa  ttcaagtgct     120
tgaaaaccac  atgtggagca  gacaagatgg  agacaaattc  ctctctcccc  acgaacatct     180
ctggagggac  acctgctgta  tctgctggct  atctcttcct  ggatatcatc  acttatctgg     240
tatttgcagt  cacctttgtc  ctcggggtcc  tgggcaacgg  gcttgtgatc  tgggtggctg     300
gattccggat  gacacacaca  gtcaccacca  tcagttacct  gaacctggcc  gtggctgact     360
tctgtttcac  ctccactttg  ccattcttca  tggtcaggaa  ggccatggga  ggacattggc     420
ctttcggctg  gttcctgtgc  aaattcgtct  ttaccatagt  ggacatcaac  ttgttcggaa     480
gtgtcttcct  gatcgccctc  attgctctgg  accgctgtgt  ttgcgtcctg  catccagtct     540
ggacccagaa  ccaccgcacc  gtgagcctgg  ccaagaaggt  gatcattggg  ccctgggtga     600
tggctctgct  cctcacattg  ccagttatca  ttcgtgtgac  tacagtacct  ggtaaaacgg     660
ggacagtagc  ctgcacttt   aactttcgc   cctggaccaa  cgaccctaaa  gagaggataa     720
atgtggccgt  tgccatgttg  acggtgagag  gcatcatccg  gttcatcatt  ggcttcagcg     780
cacccatgtc  catcgttgct  gtcagttatg  ggcttattgc  caccaagatc  cacaagcaag     840
gcttgattaa  gtccagtcgt  cccttacggg  tcctctcctt  tgtcgcagca  gcctttttc      900 tctgctggtc  cccatatcag  gtggtggccc  ttatagccac  agtcagaatc  cgtgagttat     960
tgcaaggcat  gtacaaagaa  attggtattg  cagtggatgt  gacaagtgcc  ctggccttct    1020
tcaacagctg  cctcaacccc  atgctctatg  tcttcatggg  ccaggacttc  cgggagaggc    1080
```

```
tgatccacgc ccttcccgcc agtctggaga gggccctgac cgaggactca acccaaacca    1140
gtgacacagc taccaattct actttacctt ctgcagaggt ggagttacag caaagtgag     1200 gagggagctg ggggacactt tcgagctccc agctccagct tcgtctcacc ttgagttagg    1260
ctgagccaca ggcatttcct gcttatttta ggattaccca ctcatcagaa aaaaaaaaa    1320 aagcctttgt gtccctgat ttggggagaa taaacagata tgagtttatt a             1371
```

<210> SEQ ID NO 2
<211> LENGTH: 1334
<212> TYPE: DNA
<213> ORGANISM: Homo sapiens

<400> SEQUENCE: 2

```
aatcattaga gcctgagtca ctctccccag gagacccaga cctagaacta cccagagcaa     60
gaccacagct ggtgaacagt ccaggagcag acaagatgga gacaaattcc tctctcccca    120
cgaacatctc tggagggaca cctgctgtat ctgctggcta tctcttcctg gatatcatca    180
cttatctggt atttgcagtc acctttgtcc tcggggtcct gggcaacggg cttgtgatct    240
gggtggctgg attccggatg acacacacag tcaccaccat cagttacctg aacctggccg    300
tggctgactt ctgtttcacc tccactttgc cattcttcat ggtcaggaag gccatgggag    360
gacattggcc tttcggctgg ttcctgtgca aattcgtctt taccatagtg gacatcaact    420
tgttcggaag tgtcttcctg atcgcctca ttgctctgga ccgctgtgtt tgcgtcctgc    480
atccagtctg gacccagaac caccgcaccg tgagcctggc caagaaggtg atcattgggc    540
cctgggtgat ggctctgctc ctcacattgc cagttatcat tcgtgtgact acagtacctg    600
gtaaaacggg gacagtagcc tgcactttta actttcgcc ctggaccaac gaccctaaag    660
agaggataaa tgtggccgtt gccatgttga cggtgagagg catcatccgg ttcatcattg    720
gcttcagcgc acccatgtcc atcgttgctg tcagttatgg gcttattgcc accaagatcc    780
acaagcaagg cttgattaag tccagtcgtc ccttacgggt cctctccttt gtcgcagcag    840
ccttttttct ctgctggtcc ccatatcagg tggtggccct tatagccaca gtcagaatcc    900
gtgagttatt gcaaggcatg tacaaagaaa ttggtattgc agtggatgtg acaagtgccc    960
tggccttctt caacagctgc ctcaacccca tgctctatgt cttcatgggc caggacttcc   1020
gggagaggct gatccacgcc cttcccgcca gtctggagag ggccctgacc gaggactcaa   1080
cccaaaccag tgacacagct accaattcta ctttaccttc tgcagaggtg gagttacagg   1140
caaagtgagg agggagctgg gggacacttt cgagctccca gctccagctt cgtctcacct   1200
tgagttaggc tgagccacag gcatttcctg cttattttag gattacccac tcatcagaaa   1260
aaaaaaaaaa agcctttgtg tccctgattt ggggagaat aaacagatat gagtttaaaa   1320 aaaaaaaaa aaaa                                                      1334
```

<210> SEQ ID NO 3
<211> LENGTH: 1332
<212> TYPE: DNA
<213> ORGANISM: Mus musculus

<400> SEQUENCE: 3

```
ggcttctttc ttcaggagat cagctgtaga tctgtccaga gctgttggaa agttcaggag     60
tctacaagat ggacaccaac atgtctctcc tcatgaacaa gtctgcagtg aacctcatga    120
atgtatctgg gagtactcaa tcagtatctg ctggctacat cgttctggat gtcttctcat    180
atttgatctt tgccgtcaca tttgtccttg gggttctggg caacgggctc gtgatctggg    240
```

```
tggctggttt ccgcatgaaa cacactgtca ccaccatctc ttacttgaac ttggccattg    300 ctgactttg cttcacttcc actttgccat tttacattgc cagcatggtc atgggaggac    360
attggccatt tggttggttc atgtgcaaat tcatatatac tgtaatagac ataaacctat    420 ttgaagtgt cttcctgatt gccctcattg cactggaccg ctgtatttgt gttctgcatc    480
cagtctgggc tcagaaccac cgcactgtga gcctagccaa aaggtaatc atcgtaccct    540 ggatttgtgc atttcttctt acattgccag ttatcattcg tttgaccaca gtccctaata    600
gtagacttgg accagggaaa acagcctgta ctttcgactt ctcccctgg accaaagatc    660 ctgtagagaa gaggaaggtg gccgtcacca tgctcactgt cagaggaatc atcaggttca    720
tcattgggtt cagcactccc atgtccattg ttgccatttg ctatgggtta ataaccacta    780
aaattcacag gcagggcctg atcaaatcca gccgtccttt gcgggttctc tcctttgttg    840
tggctgcctt tttcctctgc tggtgcccat tcaagtagt ggccctcata tccacaatcc    900
aagtccgtga acggttgaag aacatgactc caggcattgt aactgctttg aaaatcacaa    960
gccccttggc tttcttcaac agctgcctca atccaatgct ttatgtcttt atgggccagg    1020
acttcagaga aagactaatc cactctttac ctgccagcct agagagggcc ctgactgagg    1080
actcagctca gaccagtgat acaggcacca atttggggac caactctact tcccttttctg    1140 aaaacacttt aaatgcaatg taagaacgg gctctaactt ccagcttcat ctgctttgag    1200
ttccactgtg ctataggcat tccctgttga ccttcaggct acatgctcat taggaaaact    1260
tgaaataacc ttttagactt ttttacctca acccaagata gtcaataaag aaaaagaac    1320 ataaaaaaaa aa                                                        1332

<210> SEQ ID NO 4
<211> LENGTH: 350
<212> TYPE: PRT
<213> ORGANISM: Homo sapiens

<400> SEQUENCE: 4

Met Glu Thr Asn Ser Ser Leu Pro Thr Asn Ile Ser Gly Gly Thr Pro
1               5                   10                  15

Ala Val Ser Ala Gly Tyr Leu Phe Leu Asp Ile Ile Thr Tyr Leu Val
                20                  25                  30

Phe Ala Val Thr Phe Val Leu Gly Val Leu Gly Asn Gly Leu Val Ile
            35                  40                  45

Trp Val Ala Gly Phe Arg Met Thr His Thr Val Thr Thr Ile Ser Tyr
        50                  55                  60

Leu Asn Leu Ala Val Ala Asp Phe Cys Phe Thr Ser Thr Leu Pro Phe
65                  70                  75                  80

Phe Met Val Arg Lys Ala Met Gly Gly His Trp Pro Phe Gly Trp Phe
                85                  90                  95

Leu Cys Lys Phe Val Phe Thr Ile Val Asp Ile Asn Leu Phe Gly Ser
            100                 105                 110

Val Phe Leu Ile Ala Leu Ile Ala Leu Asp Arg Cys Val Cys Val Leu
        115                 120                 125

His Pro Val Trp Thr Gln Asn His Arg Thr Val Ser Leu Ala Lys Lys
    130                 135                 140

Val Ile Ile Gly Pro Trp Val Met Ala Leu Leu Thr Leu Pro Val
145                 150                 155                 160

Ile Ile Arg Val Thr Thr Val Pro Gly Lys Thr Gly Thr Val Ala Cys
                165                 170                 175
```

```
Thr Phe Asn Phe Ser Pro Trp Thr Asn Asp Pro Lys Glu Arg Ile Asn
                180                 185                 190

Val Ala Val Ala Met Leu Thr Val Arg Gly Ile Ile Arg Phe Ile Ile
            195                 200                 205

Gly Phe Ser Ala Pro Met Ser Ile Val Ala Val Ser Tyr Gly Leu Ile
210                 215                 220

Ala Thr Lys Ile His Lys Gln Gly Leu Ile Lys Ser Ser Arg Pro Leu
225                 230                 235                 240

Arg Val Leu Ser Phe Val Ala Ala Phe Phe Leu Cys Trp Ser Pro
                245                 250                 255

Tyr Gln Val Val Ala Leu Ile Ala Thr Val Arg Ile Arg Glu Leu Leu
            260                 265                 270

Gln Gly Met Tyr Lys Glu Ile Gly Ile Ala Val Asp Val Thr Ser Ala
            275                 280                 285

Leu Ala Phe Phe Asn Ser Cys Leu Asn Pro Met Leu Tyr Val Phe Met
            290                 295                 300

Gly Gln Asp Phe Arg Glu Arg Leu Ile His Ala Leu Pro Ala Ser Leu
305                 310                 315                 320

Glu Arg Ala Leu Thr Glu Asp Ser Thr Gln Thr Ser Asp Thr Ala Thr
                325                 330                 335

Asn Ser Thr Leu Pro Ser Ala Glu Val Glu Leu Gln Ala Lys
                340                 345                 350

<210> SEQ ID NO 5
<211> LENGTH: 350
<212> TYPE: PRT
<213> ORGANISM: Homo sapiens

<400> SEQUENCE: 5

Met Glu Thr Asn Ser Ser Leu Pro Thr Asn Ile Ser Gly Gly Thr Pro
1               5                   10                  15

Ala Val Ser Ala Gly Tyr Leu Phe Leu Asp Ile Ile Thr Tyr Leu Val
                20                  25                  30

Phe Ala Val Thr Phe Val Leu Gly Val Leu Gly Asn Gly Leu Val Ile
            35                  40                  45

Trp Val Ala Gly Phe Arg Met Thr His Thr Val Thr Thr Ile Ser Tyr
50                  55                  60

Leu Asn Leu Ala Val Ala Asp Phe Cys Phe Thr Ser Thr Leu Pro Phe
65                  70                  75                  80

Phe Met Val Arg Lys Ala Met Gly Gly His Trp Pro Phe Gly Trp Phe
                85                  90                  95

Leu Cys Lys Phe Val Phe Thr Ile Val Asp Ile Asn Leu Phe Gly Ser
                100                 105                 110

Val Phe Leu Ile Ala Leu Ile Ala Leu Asp Arg Cys Val Cys Val Leu
            115                 120                 125

His Pro Val Trp Thr Gln Asn His Arg Thr Val Ser Leu Ala Lys Lys
            130                 135                 140

Val Ile Ile Gly Pro Trp Val Met Ala Leu Leu Leu Thr Leu Pro Val
145                 150                 155                 160

Ile Ile Arg Val Thr Thr Val Pro Gly Lys Thr Gly Thr Val Ala Cys
                165                 170                 175

Thr Phe Asn Phe Ser Pro Trp Thr Asn Asp Pro Lys Glu Arg Ile Asn
                180                 185                 190

Val Ala Val Ala Met Leu Thr Val Arg Gly Ile Ile Arg Phe Ile Ile
```

```
              195                 200                 205
Gly Phe Ser Ala Pro Met Ser Ile Val Ala Val Ser Tyr Gly Leu Ile
    210                 215                 220

Ala Thr Lys Ile His Lys Gln Gly Leu Ile Lys Ser Ser Arg Pro Leu
225                 230                 235                 240

Arg Val Leu Ser Phe Val Ala Ala Phe Leu Cys Trp Ser Pro
                245                 250                 255

Tyr Gln Val Val Ala Leu Ile Ala Thr Val Arg Ile Arg Glu Leu Leu
                260                 265                 270

Gln Gly Met Tyr Lys Glu Ile Gly Ile Ala Val Asp Val Thr Ser Ala
                275                 280                 285

Leu Ala Phe Phe Asn Ser Cys Leu Asn Pro Met Leu Tyr Val Phe Met
    290                 295                 300

Gly Gln Asp Phe Arg Glu Arg Leu Ile His Ala Leu Pro Ala Ser Leu
305                 310                 315                 320

Glu Arg Ala Leu Thr Glu Asp Ser Thr Gln Thr Ser Asp Thr Ala Thr
                325                 330                 335

Asn Ser Thr Leu Pro Ser Ala Glu Val Glu Leu Gln Ala Lys
                340                 345                 350

<210> SEQ ID NO 6
<211> LENGTH: 364
<212> TYPE: PRT
<213> ORGANISM: Mus musculus

<400> SEQUENCE: 6

Met Asp Thr Asn Met Ser Leu Leu Met Asn Lys Ser Ala Val Asn Leu
1               5                   10                  15

Met Asn Val Ser Gly Ser Thr Gln Ser Val Ser Ala Gly Tyr Ile Val
                20                  25                  30

Leu Asp Val Phe Ser Tyr Leu Ile Phe Ala Val Thr Phe Val Leu Gly
            35                  40                  45

Val Leu Gly Asn Gly Leu Val Ile Trp Val Ala Gly Phe Arg Met Lys
    50                  55                  60

His Thr Val Thr Thr Ile Ser Tyr Leu Asn Leu Ala Ile Ala Asp Phe
65                  70                  75                  80

Cys Phe Thr Ser Thr Leu Pro Phe Tyr Ile Ala Ser Met Val Met Gly
                85                  90                  95

Gly His Trp Pro Phe Gly Trp Phe Met Cys Lys Phe Ile Tyr Thr Val
                100                 105                 110

Ile Asp Ile Asn Leu Phe Gly Ser Val Phe Leu Ile Ala Leu Ile Ala
            115                 120                 125

Leu Asp Arg Cys Ile Cys Val Leu His Pro Val Trp Ala Gln Asn His
    130                 135                 140

Arg Thr Val Ser Leu Ala Lys Lys Val Ile Ile Val Pro Trp Ile Cys
145                 150                 155                 160

Ala Phe Leu Leu Thr Leu Pro Val Ile Ile Arg Leu Thr Thr Val Pro
                165                 170                 175

Asn Ser Arg Leu Gly Pro Gly Lys Thr Ala Cys Thr Phe Asp Phe Ser
            180                 185                 190

Pro Trp Thr Lys Asp Pro Val Glu Lys Arg Lys Val Ala Val Thr Met
    195                 200                 205

Leu Thr Val Arg Gly Ile Ile Arg Phe Ile Ile Gly Phe Ser Thr Pro
210                 215                 220
```

```
Met Ser Ile Val Ala Ile Cys Tyr Gly Leu Ile Thr Thr Lys Ile His
225                 230                 235                 240

Arg Gln Gly Leu Ile Lys Ser Ser Arg Pro Leu Arg Val Leu Ser Phe
                245                 250                 255

Val Val Ala Ala Phe Phe Leu Cys Trp Cys Pro Phe Gln Val Val Ala
            260                 265                 270

Leu Ile Ser Thr Ile Gln Val Arg Glu Arg Leu Lys Asn Met Thr Pro
        275                 280                 285

Gly Ile Val Thr Ala Leu Lys Ile Thr Ser Pro Leu Ala Phe Phe Asn
    290                 295                 300

Ser Cys Leu Asn Pro Met Leu Tyr Val Phe Met Gly Gln Asp Phe Arg
305                 310                 315                 320

Glu Arg Leu Ile His Ser Leu Pro Ala Ser Leu Glu Arg Ala Leu Thr
                325                 330                 335

Glu Asp Ser Ala Gln Thr Ser Asp Thr Gly Thr Asn Leu Gly Thr Asn
                340                 345                 350

Ser Thr Ser Leu Ser Glu Asn Thr Leu Asn Ala Met
            355                 360
```

```
<210> SEQ ID NO 7
<211> LENGTH: 20
<212> TYPE: DNA
<213> ORGANISM: Artificial Sequence
<220> FEATURE:
<223> OTHER INFORMATION: FPR 1 forward primer

<400> SEQUENCE: 7
ccttggcttt cttcaacagc                                          20

<210> SEQ ID NO 8
<211> LENGTH: 20
<212> TYPE: DNA
<213> ORGANISM: Artificial Sequence
<220> FEATURE:
<223> OTHER INFORMATION: FPR 1 backward primer

<400> SEQUENCE: 8
gcccgttctt tacattgcat                                          20

<210> SEQ ID NO 9
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 9
gcccgttctt tacattgcat                                          20

<210> SEQ ID NO 10
<211> LENGTH: 20
<212> TYPE: DNA
<213> ORGANISM: Artificial Sequence
<220> FEATURE:
<223> OTHER INFORMATION: GAPDH backward primer

<400> SEQUENCE: 10
ttgatggcaa caatctccac                                          20
```

SCREENING METHOD FOR THERAPEUTIC SUBSTANCE FOR PREVENTING OR TREATING BRONCHOPULMONARY DYSPLASIA (BPD)

CROSS-REFERENCE TO RELATED APPLICATIONS

This application is a national phase application of PCT Application No. PCT/KR2019/005365, filed on May 3, 2019, which claims priority to Korean Patent Application Nos. 10-2018-0051692, filed on May 4, 2018 and 10-2019-0052188, filed on May 3, 2019. The entire disclosure of the applications identified in this paragraph is incorporated herein by reference.

FIELD

The present invention relates to a screening method for a therapeutic agent for pulmonary damage symptoms induced by the administration of high-concentration oxygen, and more specifically, to a screening method for a candidate material for a therapeutic agent for bronchopulmonary dysplasia (BPD) induced by high-concentration oxygen.

BACKGROUND

Formyl peptide receptor 1 (FPR1) is a cell surface receptor protein, and is widely expressed in blood neutrophils, eosinophils, basophils, monocytes, and platelets; tissue-bound macrophages, fibroblasts, and immature dendritic cells; vascular endothelium and smooth muscle cells; various forms of epithelial cells, hepatocytes, neural tissue glial cells, astrocytes and malignant neuroblastoma cells; keratinocytes; and virtually all types of multicellular tissues. FPR1 binds to a bacterial or mitochondrial N-formyl peptide, and is then activated by the N-formyl peptide to initiate an innate host immune response.

Meanwhile, bronchopulmonary dysplasia (BPD) occurs when immature lungs are exposed to high concentrations of oxygen, there is no clear treatment method for BPD, and as a known treatment method to date, physical methods have been mainly made to reduce the pressure and oxygen concentration by positive pressure ventilation in treatment of artificial ventilation of neonates and premature infants, and furthermore, there is a steroid therapy which is a treatment of reducing damaged lung inflammation, but when this treatment is used in premature infants, there have been reports that the treatment is associated with an increase in neurologically poor prognoses, especially cerebral palsy, and thus the use thereof is limited (Committee on Fetus and Newborn, Pediatrics, 109:330-8, 2002).

As described above, although there is no suitable treatment method, premature infant survival treatment techniques have been developed, so that premature infant survival rates have been increased, and for this reason, the frequency of bronchopulmonary dysplasia is expected to continuously increase.

Therefore, although research and development have been actively conducted in order to develop a treatment method for bronchopulmonary dysplasia, there is an urgent need for developing a therapeutic agent suitable for bronchopulmonary dysplasia because there is still no effective treatment method.

SUMMARY

Technical Problem

The present inventors have discovered that FPR1 is over-expressed in lung tissues exposed to high-concentration oxygen, and as a result of focusing on the correlation between the expression of FPR1 and the development of BPD, have confirmed that BPD can be suppressed by inhibiting the expression or activity of FPR1, thereby completing the present invention.

Therefore, an object of the present invention is to provide a screening method of a material which reduces the expression or activity of FPR1 compared to a non-treatment group by treating cells exhibiting bronchopulmonary dysplasia (BPD) conditions with a candidate material, and measuring the expression or activity of FPR1 in the cells after treatment of the candidate material.

However, technical problems to be achieved by the present invention are not limited to the aforementioned problems, and other problems that are not mentioned may be clearly understood by those skilled in the art from the following description.

Technical Solution

To achieve the above object, the present invention provides a screening method for a material for preventing or treating bronchopulmonary dysplasia (BPD), the method including: the following steps.

(a) treating cells exhibiting bronchopulmonary dysplasia (BPD) conditions with a candidate material; (b) measuring the expression or activity of formyl peptide receptor1 (FPR1) in the cells after treatment of the candidate material; and (c) selecting a material which reduces the expression or activity level of FPR1 compared to a non-treatment group as a material for preventing or treating bronchopulmonary dysplasia (BPD).

As an exemplary embodiment of the present invention, the candidate material may be selected from the group consisting of compounds, microbial culture media or extracts, natural product extracts, nucleic acids and peptides.

As another exemplary embodiment of the present invention, the FPR1 gene may be any one selected from the group consisting of nucleotide sequences represented by SEQ ID NO: 1, SEQ ID NO: 2, and SEQ ID NO: 3.

As still another exemplary embodiment of the present invention, the FPR1 may be any one selected from the group consisting of amino acid sequences represented by SEQ ID NO: 4, SEQ ID NO: 5, and SEQ ID NO: 6.

As yet another exemplary embodiment of the present invention, Step (b) may be measured using one or more methods selected from the group consisting of immunoprecipitation, immunohistochemistry, microarray, northern blotting, western blotting, enzyme-linked immunosorbent assay (ELISA), polymerase chain reaction (PCR), and immunofluorescence.

Advantageous Effects

The present inventors have discovered that FPR1 is over-expressed in lung tissues exposed to high-concentration oxygen, and as a result of focusing on the correlation between the expression of FPR1 and the development of BPD, have confirmed that BPD can be suppressed by inhibiting the expression or activity of FPR1. In view of this fact, a prophylactic or therapeutic material for BPD can be discovered in a rapid and accurate manner by checking whether the expression or activity level of FPR1 is inhibited, and thus, the screening method of the present invention can be beneficially used to effectively develop and select therapeutic agents for BPD.

DETAILED DESCRIPTION

Figure 1:
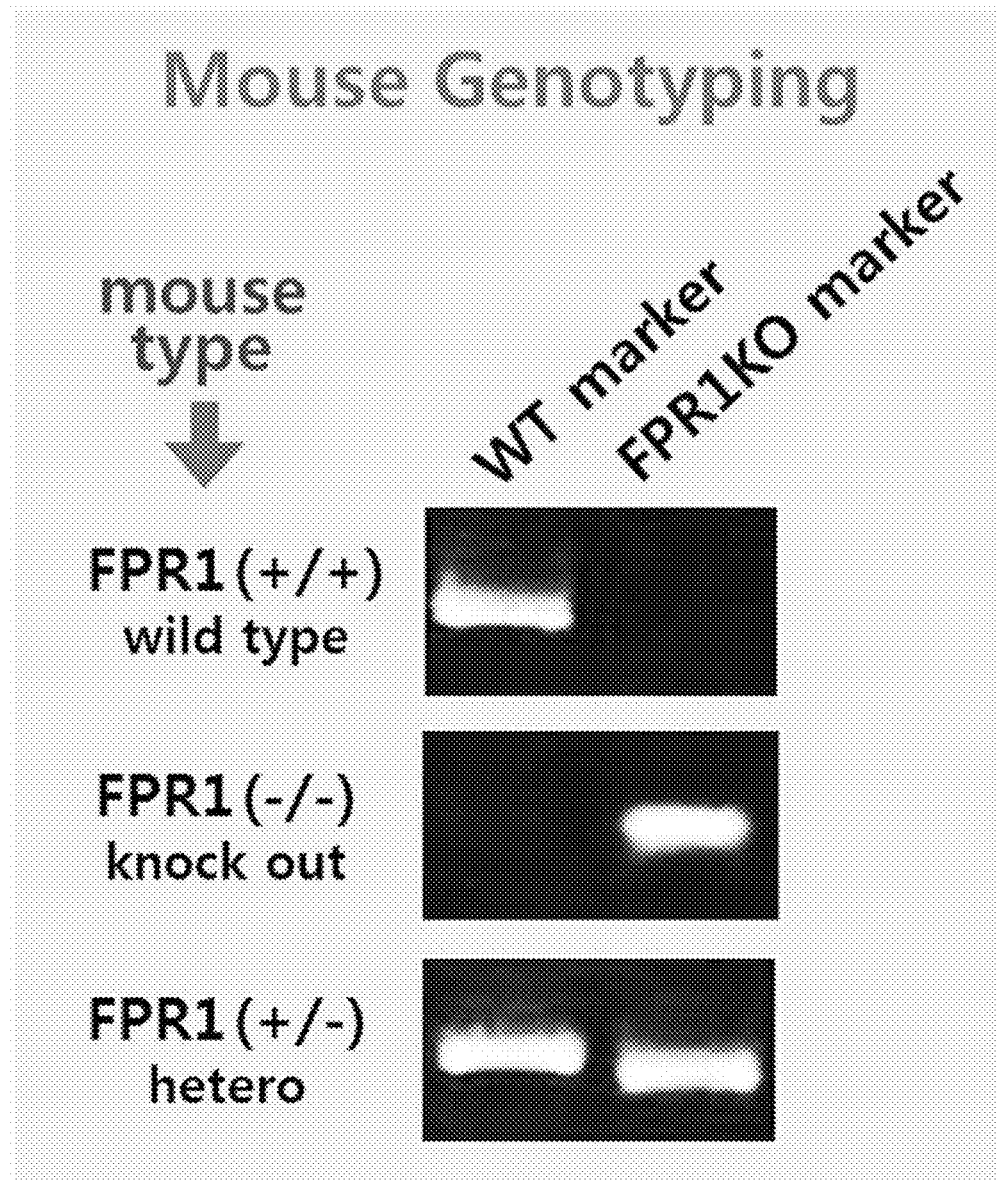
FIG. 1 illustrates the results of FPR1 genotyping of a wild type (WT), an FPR1 knockout model (FPR1KO), and an FPR1 hetero model (FPR1hetero).

Hereinafter, the present invention will be described in detail.

The present invention provides a screening method for a material for preventing or treating bronchopulmonary dysplasia (BPD).

While studying the cause of bronchopulmonary dysplasia (BPD), the present inventors have discovered that FPR1 is over-expressed in lung tissues administered high-concentration oxygen, and have confirmed that when a candidate material (for example, human umbilical cord blood-derived mesenchymal stem cells) suppresses FPR1, pathological symptoms associated with bronchopulmonary dysplasia are suppressed, thereby completing the present invention.

In an exemplary embodiment of the present invention, as a result of confirming the FPR1 expression levels of a wild type and an FPR1 knockout model when exposed to normal oxygen or high-concentration oxygen, the present inventors have confirmed that the relative expression amount of FPR1 mRNA in lung tissues is significantly higher in a wild type to which high-concentration oxygen is administered than in a wild type to which normal oxygen is administered, and that the relative expression amount of mRNA is significantly smaller in an FPR1 knockout administered high-concentration oxygen than in the wild type group administered high-concentration oxygen (see Example 2-1).

Further, in another exemplary embodiment of the present invention, from the morphological aspect of the pulmonary alveoli, the present inventors have confirmed that the pulmonary alveoli of the wild type to which high-concentration oxygen is administered are not dense and show a swollen form compared to a wild type to which normal oxygen is administered, and that the FPR1 knockout to which high-concentration oxygen is administered shows a morphology more similar to the pulmonary alveoli of the wild type to which normal oxygen is administered than the wild type group to which high-concentration oxygen is administered (see Example 2-2).

In addition, as a result of measuring mean linear intercepts and alveolar volumes, the present inventors have confirmed that the mean linear intercept and alveolar volume of the wild type to which high-concentration oxygen is administered is significantly larger than those of the wild type to which normal oxygen is administered, and that the mean linear intercept and alveolar volume of the FPR1 knockout to which high-concentration oxygen is administered are significantly smaller than those of the wild type group to which high-concentration oxygen is administered (see Example 2-2).

Furthermore, in still another exemplary embodiment of the present invention, as a result of performing an experiment which confirms cell death in lung tissues, the present inventors have confirmed that the number of dead cells in lung tissues of a wild type to which high-concentration oxygen is administered is significantly higher than that of dead cells in lung tissues of a wild type to which normal oxygen is administered, and that the number of dead cells in lung tissues of an FPR1 knockout to which high-concentration oxygen is administered is smaller than that of the wild type group to which high-concentration oxygen is administered (see Example 2-3).

Further, in yet another exemplary embodiment of the present invention, as a result of performing an experiment which confirms indices associated with inflammation, the present inventors have confirmed that the macrophage activity in lung tissues of a wild type to which normal oxygen is administered is significantly higher than that of a wild type to which normal oxygen is administered, and that the microphage activity in an FPR1 knockout to which high-concentration oxygen is administered is significantly lower than that in the wild type group to which high-concentration oxygen is administered (see Example 2-4).

In addition, as a result of measuring the activity of myeloperoxidase (MPO), which is an index of neutrophil accumulation, the present inventors have confirmed that the MPO activity in lung tissues of a wild type to which high-concentration oxygen is administered is significantly higher than that of a wild type to which normal oxygen is administered, and that the MPO activity in an FPR1 knockout to which high-concentration oxygen is administered is significantly lower than that of the wild type group to which high-concentration oxygen is administered (see Example 2-4).

Furthermore, in yet another exemplary embodiment of the present invention, as a result of performing an experiment which confirms angiogenesis in lung tissues, the present inventors have confirmed that angiogenesis in lung tissues of a wild type to which high-concentration oxygen is administered is significantly lower than that of a wild type to which normal oxygen is administered, and that angiogenesis in lung tissues of an FPR1 knockout to which high-concentration oxygen is administered is significantly larger than that of the wild type group to which oxygen is administered (see Example 2-5).

The above results have confirmed that in the case of an FPR1 knockout animal model, the expression of FPR1 is lower than that of a wild type, and unlike the wild type, even though high-concentration oxygen is administered, angiogenesis is increased while conditions associated with bronchopulmonary dysplasia, that is, the morphological changes of lung tissues, the occurrence of cell death, and the inflammation occurrence level of lung tissues are low.

The above-described exemplary embodiments have verified that the expression level of FPR1 is involved in the onset of bronchopulmonary dysplasia, and from this, it could be confirmed that when the expression level of FPR1 is low, the onset of bronchopulmonary dysplasia is suppressed.

Therefore, the above-described present invention provides a screening method for a material for preventing or treating bronchopulmonary dysplasia (BPD), the method including: the following steps.
  (a) treating cells exhibiting bronchopulmonary dysplasia (BPD) conditions with a candidate material;
  (b) measuring the expression or activity of FPR1 in the cells after treatment of the candidate material; and
  (c) selecting a material which reduces the expression or activity level of FPR1 compared to a non-treatment group as a material for preventing or treating bronchopulmonary dysplasia (BPD).

In the present invention, FPR1 is a cell surface receptor protein encoded by formyl peptide receptor 1 (FPR1) in humans. FPR1 encodes a G protein-coupled receptor cell surface protein which is a high affinity receptor which is activated and bound by N-formylmethionine-containing oligopeptides which are strong neutrophil chemotactic factors, particularly, N-formylmethionine-leucyl-phenylalanine (FMLP). FPR1 is expressed in mammalian phagocytes and blood leukocytes, and mediates a series of cellular responses after binding to N-formylmethionine-containing oligopeptides released from invading microorganisms and damaged tissues. Further, Fpr1 is a human FPR1 protein ortholog of a mouse (Mus musculus), and is a cell surface receptor protein encoded by Fpr1 which is an ortholog gene of human Fpr1.

The FPR1 gene (FPR1) according to the present invention may include a nucleotide sequence represented by SEQ ID NO: 1 (NCBI Accession: NM_001193306.1), SEQ ID NO: 2 (NCBI Accession: NM_002029.3), or SEQ ID NO: 3 (NCBI Accession: NM_013521.2), and FPR1 may include an amino acid sequence represented by SEQ ID NO: 4 (NCBI Accession: NP_001180235.1), SEQ ID NO: 5 (NCBI Accession: NP_002020.1), or SEQ ID NO: 6 (NCBI Accession: NP_038549.1). In this case, it is possible to include a nucleotide sequence having a sequence homology of 70% or more, preferably 80% or more, more preferably 90% or more, and most preferably 95%, 96%, 97%, 98%, or 99% or more with the nucleotide sequences represented by SEQ ID NO: 1 to 3.

As used herein, a candidate material refers to a material expected to suppress the expression or activity level of FPR1, and the candidate material may include a natural product extract or a single compound isolated from the natural product extract, and may be a compound, a microbial culture medium or extract, a natural product extract, a nucleic acid, and a peptide, but is not limited thereto.

In the present invention, the target disease bronchopulmonary dysplasia (BPD) is a chronic lung disease occurring in patients who have received artificial ventilation therapy and oxygen treatment due to neonatal respiratory distress syndrome, and often occurs in premature infants who have a low gestational age and a low birth weight. Some very low birth weight infants require artificial ventilation therapy due to apnea or respiratory failure without neonatal respiratory distress syndrome, and bronchopulmonary dysplasia may occur even in this case. Bronchopulmonary dysplasia may be usually defined as a case requiring oxygen supply even after a gestational period of 36 weeks, and is classified into mild, moderate, and severe depending on the degree of required oxygen. A recent study reported that the frequency of bronchopulmonary dysplasia was 42% at a birth weight of 510 to 750 g, 25% at a birth weight of 751 to 1000 g, 11% at a birth weight of 1001 to 1250 g, and 5% at a birth weight of 1251 to 1500 g, based on 36 weeks after the last menstruation before pregnancy.

In the present invention, Step (a) may be a step of treating a bronchopulmonary dysplasia (BPD) disease animal model itself or cells derived from the bronchopulmonary dysplasia (BPD) disease animal model with a candidate material.

In the present invention, Step (b) may be measured using one or more methods selected from the group consisting of immunoprecipitation, immunohistochemistry, microarray, northern blotting, western blotting, enzyme-linked immunosorbent assay (ELISA), polymerase chain reaction (PCR), and immunofluorescence.

Hereinafter, preferred examples for helping the understanding of the present invention will be suggested. However, the following examples are provided only to more easily understand the present invention, and the contents of the present invention are not limited by the following examples.

EXAMPLES

Example 1. Experimental Preparation and Experimental Methods 1-1. Preparation of Tissues After mice were anesthetized using pentobarbital (60 mg/kg, i.p.), the lungs of the mice were removed immediately after transcardiac perfusion in ice cold PBS. Tissue preparation for PCR and histology was prepared from other mouse pups. For lung morphometry and immunohistochemistry, the extracted lung tissues were expanded using PBS at a constant expansion pressure of 20 cm $H_2O$, and then fixed by immersion. A lung tissue paraffin block was cut into 4 µm cross-sections. The lungs were rapidly frozen in liquid nitrogen for biochemical observation, and stored at −80° C. until use.

1-2. Measurement of FPR1 mRNA Expression

The FPR1 mRNA expression levels in the lung tissues were measured by reverse transcription-PCR (RT-PCR).

First, total RNA was isolated from homogenized lung tissues using a TRIzol reagent (Invitrogen, La Jolla, CA, USA) according to the manufacturer's instructions.

Complementary DNA (cDNA) was synthesized from the total RNA using SMART Scribe Reverse Transcriptase (Clontech, Tokyo, Japan) and pd(N) 6 random hexamer (Bioneer, Daejeon, Korea) according to the manufacturer's instructions.

Using 1 microliter of cDNA (250 ng/μl), PCR was performed under the following conditions to amplify FPR1 and GAPDH as a housekeeping gene. Heating was started at 94° C. for 5 minutes, followed by 32 cycles of 94° C. for 30 seconds, 57° C. for 30 seconds, and 72° C. for 30 seconds. The primer sequences used are shown in the following Table 1.

TABLE 1

| Classification | Forward | Reverse |
| --- | --- | --- |
| FPR1 Primer Sequence | 5'-CCTTGGCTTTCTTCAACAGC-3' (SEQ ID NO: 7) | 5'-GCCCGTTCTTTACATTGCAT-3' (SEQ ID NO: 8) |
| GAPDH Primer Sequence | 5'-GCCCGTTCTTTACATTGCAT-3' (SEQ ID NO: 9) | 5'-TTGATGGCAACAATCTCCAC-3' (SEQ ID NO: 10) |

Finally, PCR products were analyzed and visualized with E-Gel Power Snap Electrophoresis System (Invitrogen, Massachusetts, USA). PCR band intensities of FPR1 and GAPDH were measured using ImageJ software (National Institutes of Health, Bethesda, MD), and used to calculate an FPR1/GAPDH ratio.

1-3. Lung Morphometry

Paraffin-embedded lung sections (4 μm thick sections) were stained with hematoxylin and eosin. The sizes of pulmonary alveoli were evaluated by mean linear intercept (MLI), mean alveolar volume (MAV) and radial alveolar count (RAC). At least 6 non-overlapping microfields (200× magnification, MLI and MAV, 35× magnification, RAC) were randomly selected for morphological measurements.

1-4. Immunohistochemistry

Paraffin-embedded lung sections were immunostained with CD68 (1:100, ab31630, Abcam, Cambridge, UK) and myeloperoxidase (MPO) (1:25; ab9535, Abcam) primary antibodies for histological analysis of inflammation. The numbers of CD68-positive alveolar macrophages and MPO-positive polymorphonuclear neutrophils were counted at 200× magnification in at least 6 non-overlapping regions.

Further, for histological analysis of angiogenesis, lung sections were immunostained for a vascular endothelial cell marker, von Willebrand factor (vWF) (immune system; IR527, FLEX, Dako, Glostrup, Denmark). In order to quantify angiogenesis, the light intensity of vWF-positive cells was counted at 100× magnification in at least 6 or more non-overlapping regions using ImageJ software (National Institutes of Health, Bethesda, MD). All quantifications of the histological analyses were performed in blind observer mode.

1-5. Enzyme-Linked Immunosorbent Assay

After homogenization and centrifugation of frozen lung tissues, the protein concentration of each supernatant was standardized across all samples. VEGF levels were measured using a commercially-available enzyme-linked immunosorbent assay (ELISA) (VEGF-R&D Systems, Minneapolis, MN, USA).

1-6. Western Blot

CD31 and caspase 9 were detected in lung tissues by performing western blot for biochemical analysis of angiogenesis and cell death (apoptosis). First, after a membrane was blocked and cultured with primary antibodies against CD31 (1:1000; sc-376764, Santa Cruz Biotechnology, Santa Cruz, CA, USA) and caspase 9 (1:500; sc-7885, Santa Cruz Biotechnology), the membrane was cultured using a secondary antibody (1:1,000, DAKO). As a loading control, the level of a housekeeping protein, glyceraldehyde-3-phosphate dehydrogenase (GAPDH, 1:1000, sc-25778, Santa Cruz Biotechnology), was measured.

Protein signals were amplified using an ECL Prime Western blotting detection reagent (GE Healthcare, Piscataway, NJ, USA) and detected using Amersham Imager 600 (GE Healthcare Life Sciences, Pittsburgh, USA). The intensity of a detected band was measured using ImageJ software (National Institutes of Health, Bethesda, MD, USA), and the ratio of labeled protein/GAPDH was calculated from the band intensity.

1-7. TUNEL Staining

In order to observe the cell death of lung tissues, TUNEL staining was performed on lung sections using a DeadEnd Fluorometric TUNEL system kit (G3250; Promega, Madison, WI). TUNEL-stained lung sections were observed at 200× magnification. The number of TUNEL positive cells was counted in 6 or more non-overlapping regions and the counting was performed in blind observer mode.

1-8. Statistical Analysis

Data are shown as mean±SEM. After a normal distribution was verified, a mean linear intercept, which is the most important morphological parameter of toxic pulmonary damage in the wild type high-concentration oxygen administration group (n=8) and the FPR1 knockout high-concentration oxygen administration group (n=6), was dynamically calculated and analyzed. When the significance level (a) is set to 0.05 and the power is set to 0.8, group sample sizes 8 and 6 obtain a statistical power of 81%. The results showed that 6 to 8 subjects were sufficient for the study. For continuous variables, statistical comparisons between groups were performed by one-way analysis of variance (ANOVA) and Tukey's post hoc analysis. All data were analyzed using SAS 9.4 software (SAS Institute, Cary, NC) and P values less than 0.05 were considered to be statistically significant.

1-9. Production of Bronchopulmonary Dysplasia Model

All animal experiments were approved by the Research Animal Laboratory Committee of Samsung Biomedical Research Institute, Korea and followed institutional guidelines.

First, in order to produce a bronchopulmonary dysplasia model, pregnant C57BL6 mice (DBL Co., Ltd.) whose gestational age was exactly known were purchased and then bred for at least 1 week or more before delivery in an experimental animal breeding facility. High-concentration oxygen was administered to neonatal mice born from this for 14 days immediately after birth (within 10 hours after birth).

Specifically, high-concentration pulmonary damage was induced by exposing a cage including mother mice and mouse pups in an acrylic can with a size of 36×28×30.0 cm (sealed Plexiglas cage) to 80% high-concentration oxygen for 14 days. Humidity and temperature (room temperature) were kept constant. In order to prevent oxygen toxicity in the mother mice, the mother mice were bred while being alternately moved to a cage at normoxia concentration and a cage at 80% high-concentration oxygen in a 24-hour cycle.

1-10. Production of FPR1 Knockout Animal Model

FPR1 knockout mice were produced by a method of removing a 50-bp open reading frame (ORF) sequence fragment important for FPR1 gene expression (Reference: JExp Med. 1999 Feb. 15; 189(4):657-62). FPR1 gene expression patterns of the wild type (WT), FPR1 knockout model (FPR1KO), and FPR1 hetero model (FPR1 hetero) were confirmed by a PCR method using marker primers for the wild type and the FPR1 knockout, respectively, and this is as shown in FIG. 1.

1-11. Preparation of Experimental Groups

Six to eight animals for each of experimental groups, which are ① wild type normoxia group (wild type_normoxia control, WT-NC), ② wild type high-concentration oxygen administration group (wild type_hyperoxia control, WT-HC), ③ FPR1 knockout high-concentration oxygen administration group (FPR1KO_hyperoxia control, FPR1KO-HC), were prepared for the experiment.

Example 2. Confirmation of Changes in Lung Tissues During High-Concentration Oxygen Administration in Wild Type (WT) and FPR1 Knockout Model (FPR1KO)

An experiment confirming the expression level of FPR1, the morphology and volume of the pulmonary alveoli, cell death, and the changes in inflammation and angiogenesis was performed by producing a model in which FPR1 was knocked out in order to suppress FPR1.

2-1. Confirmation of Changes in FPR1 Expression Levels in Wild Type (WT) and FPR1 Knockout Model (FPR1KO)

An experiment for confirming the presence or absence of FPR1 mRNA expression and the relative expression level of FPR1 was performed using the experimental groups of Example 1-11.

Figure 2:
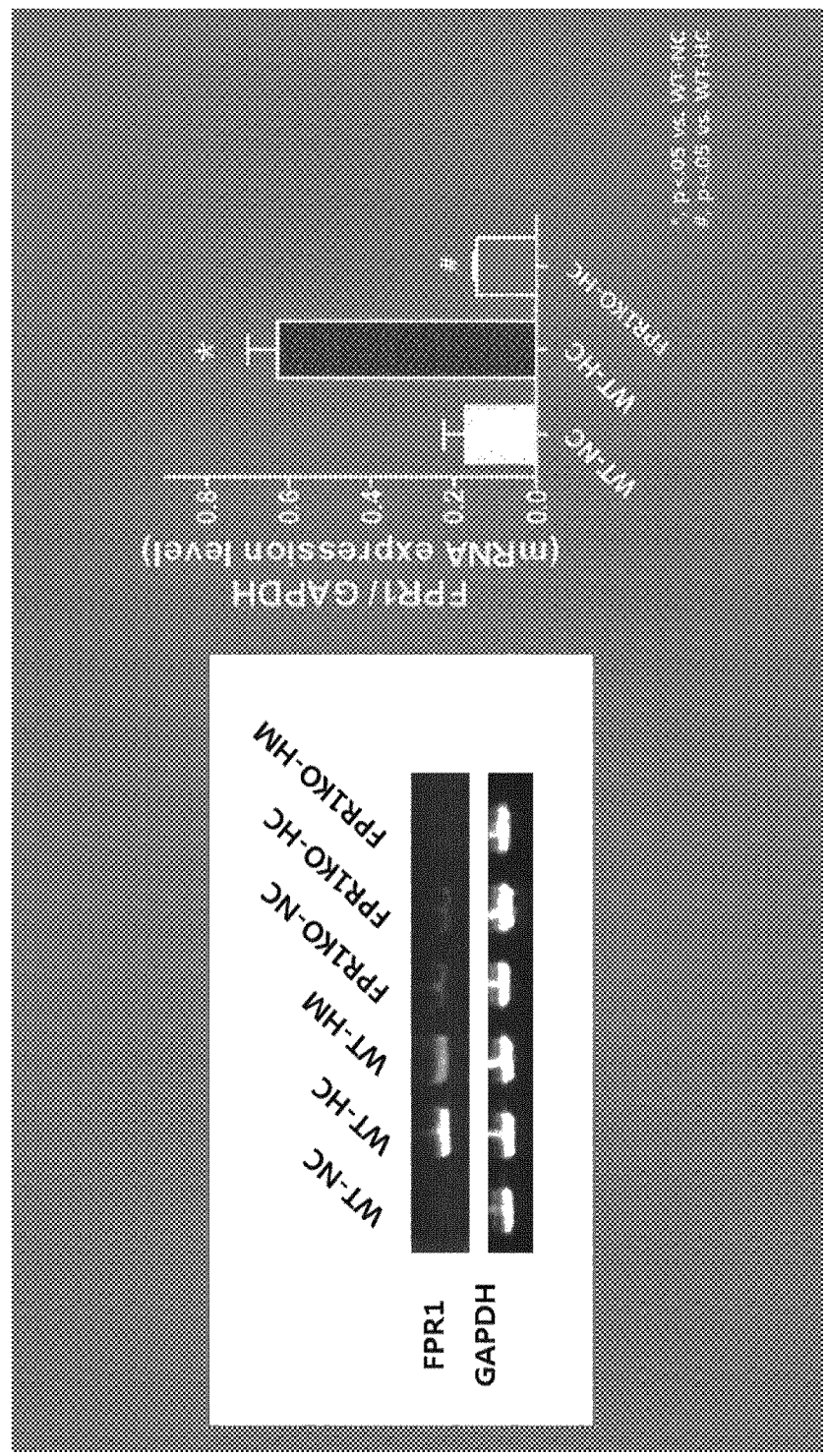
FIG. 2 illustrates the results of confirming the presence or absence of expression of and the expression amount of FPR1 mRNA in a wild type (WT) and an FPR1 knockout model (FPR1KO) under normoxia conditions and high-concentration oxygen administration conditions.

As a result, as illustrated in FIG. 2, it was confirmed that the mRNA relative expression amount of FPR1 in lung tissues was significantly larger in the wild type hyperoxia control (WT-HC) than that in the wild type normoxia control (WT-NC) ($P<0.05$).

Further, it was confirmed that the mRNA relative expression amount of FPR1 was significantly smaller in an FPR1 knockout hyperoxia control (FPR1KO-HC) than that in the wild type hyperoxia control (WC-HC) ($P<0.05$).

2-2. Confirmation of Changes in Pulmonary Alveoli in Wild Type (WT) and FPR1 Knockout Model (FPR1KO)

An experiment for confirming the morphology of the pulmonary alveoli and the circumference and volume of the pulmonary alveoli was performed using the experimental groups of Example 1-11.

Figure 3A:
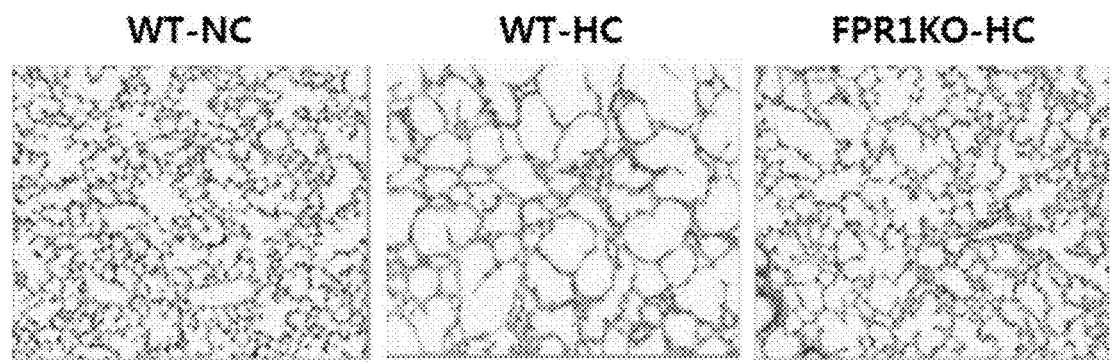
FIG. 3A illustrates the results of staining the pulmonary alveoli of a wild type (WT) and an FPR1 knockout model (FPR1KO) under normoxia conditions and high-concentration oxygen administration conditions.

As a result, as illustrated in FIG. 3A, it was confirmed that the pulmonary alveoli of the wild type hyperoxia control (WT-HC) are not dense and show a swollen form compared to the wild type normoxia control (WT-NC).

Further, it was confirmed that the FPR1 knockout hyperoxia control (FPR1KO-HC) shows a morphology more similar to the pulmonary alveoli of the wild type normoxia control than the wild type hyperoxia control (WT-HC).

Figure 3B:
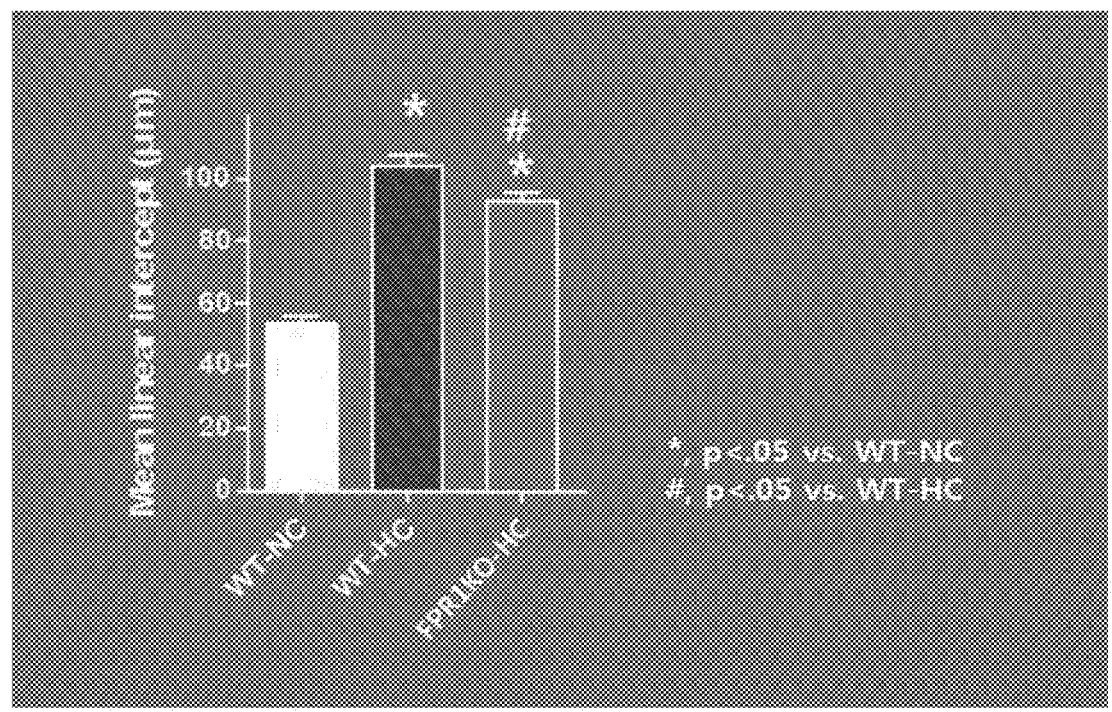
FIG. 3B illustrates the mean linear intercepts of a wild type (WT-NC) under normoxia conditions, a wild type (WT-HC) under high-concentration oxygen administration conditions, and an FPR1 knockout model (FPR1KO-HC) under high-concentration oxygen conditions.
Figure 3C:
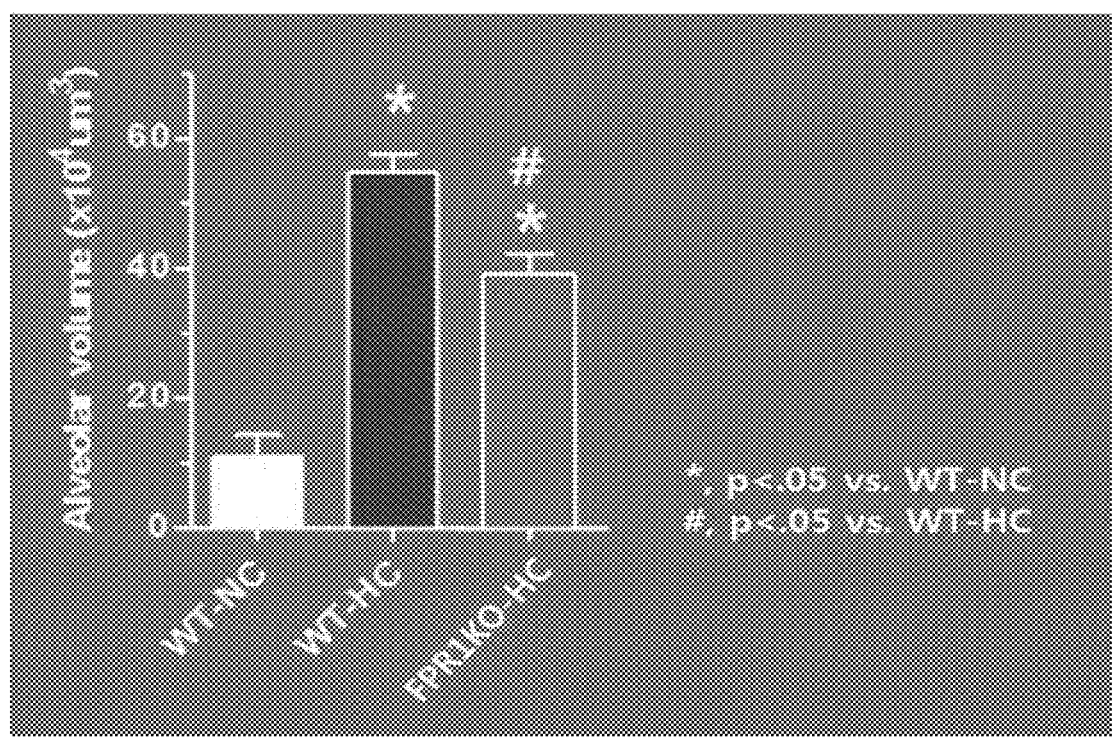
FIG. 3C illustrates the results of measuring the alveolar volumes of pulmonary alveoli of a wild type (WT-NC) under normoxia concentrations, a wild type (WT-HC) under high-concentration oxygen administration conditions, and an FPR1 knockout model (FPR1KO-HC) under high-concentration oxygen conditions.

Meanwhile, as a result of measuring the mean linear intercept and alveolar volume in order to confirm the structure of the lungs, as illustrated in FIGS. 3B and 3C, it was confirmed that the mean linear intercept and alveolar volume of the wild type hyperoxia control (WT-HC) are significantly larger than those of the wild type normoxia control (WT-NC) ($P<0.05$).

Further, it was confirmed that the mean linear intercept and alveolar volume of the FPR1 knockout hyperoxia control (FPR1KO-HC) are significantly smaller than those of the wild type hyperoxia control (WT-HC) even though they are significantly larger than those of the wild type normoxia control (WT-NC) ($P<0.05$).

The results coincide with results of observing the morphology of the pulmonary alveoli observed in the above-described wild type hyperoxia control.

2-3. Confirmation of Cell Death in Wild Type (WT) and FPR1 Knockout Model (FPR1KO)

An experiment for confirming the degree of cell death in lung tissues was performed using the experimental groups of Example 1-11.

Figure 4:
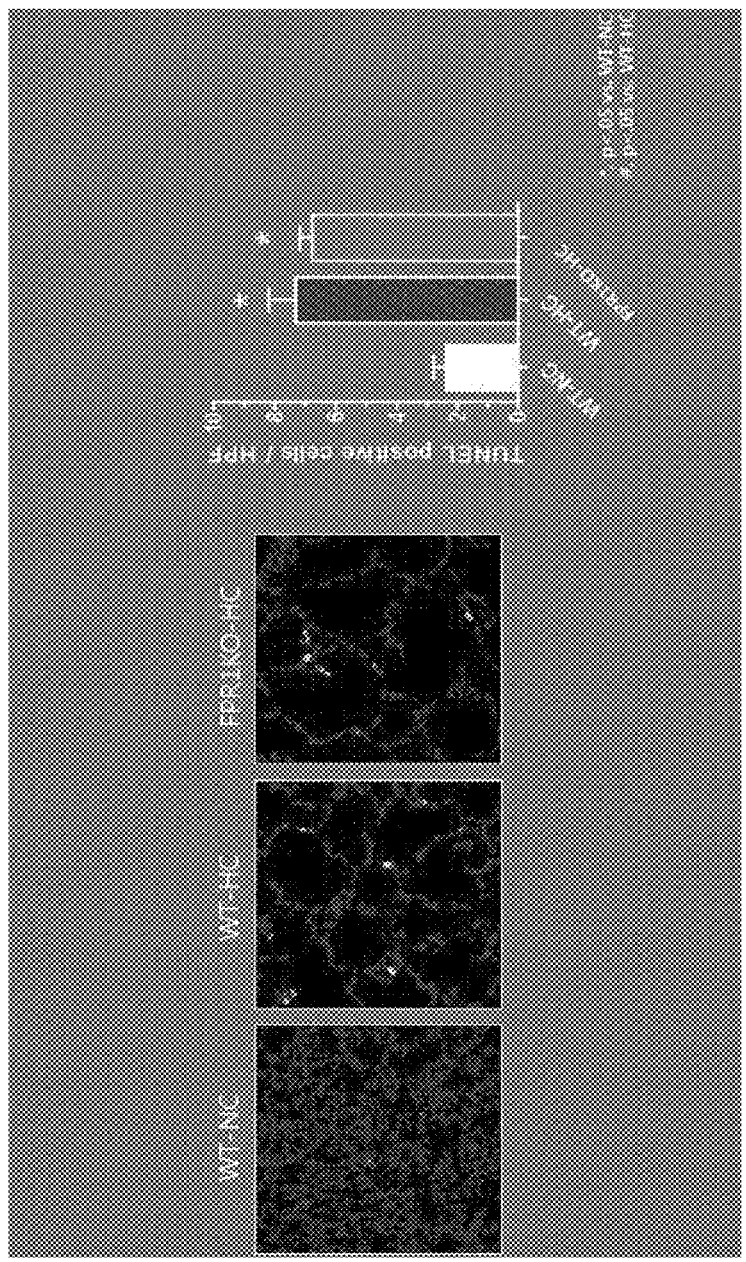
FIG. 4 illustrates the results of confirming TUNEL apoptotic cell detection of a wild type (WT) and an FPR1 knockout model (FPR1KO) under normoxia conditions and under high-concentration oxygen administration conditions.

As a result, as illustrated in FIG. 4, it was confirmed that the number of dead cells in lung tissues of the wild type hyperoxia control (WT-HC) is significantly larger than that of the wild type normoxia control (WT-NC) ($P<0.05$).

In addition, it was confirmed that the number of dead cells in lung tissues of the FPR1 knockout hyperoxia control (FPR1KO-HC) is smaller than that of the wild type hyperoxia control (WT-HC), even though it is significantly larger than that of the wild type normoxia control (WT-NC).

2-4. Confirmation of Onset of Inflammation in Wild Type (WT) and FPR1 Knockout Model (FPR1KO)

An experiment for confirming the activity of CD68-positive alveolar macrophages was performed using the experimental groups of Example 1-11.

Figure 5:
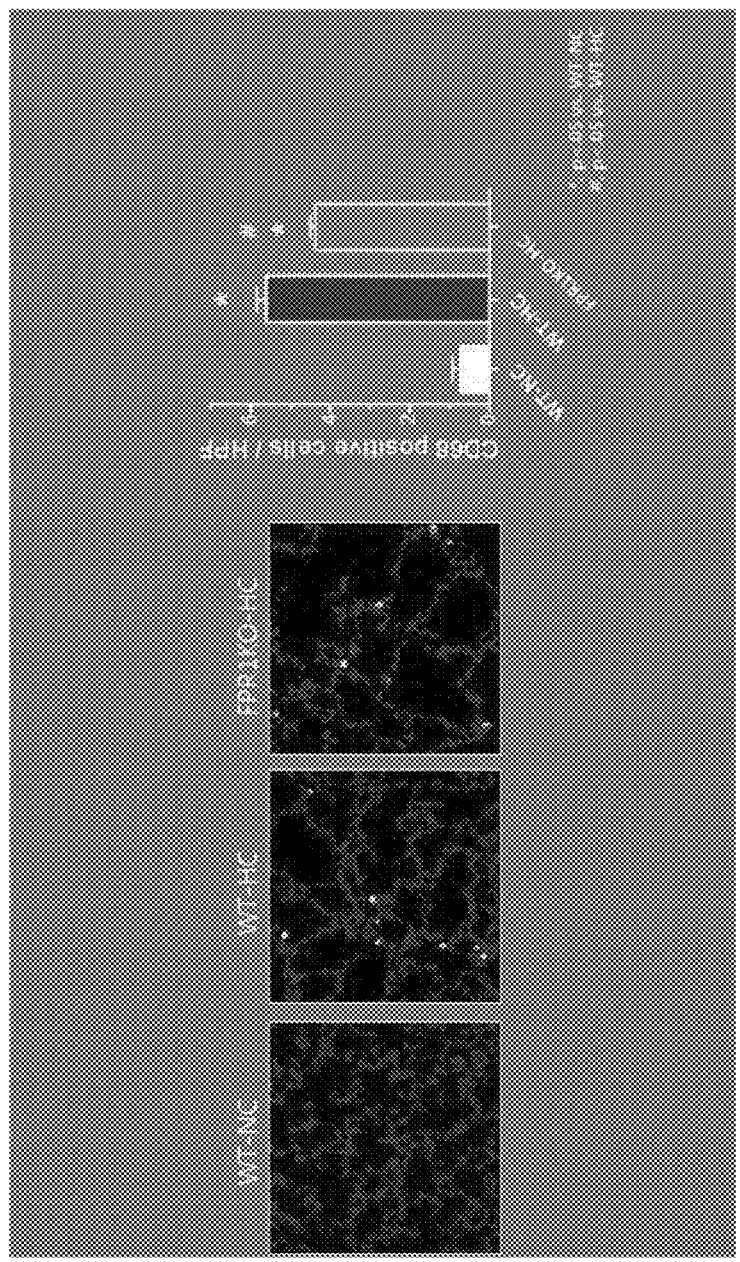
FIG. 5 illustrates the results of confirming the CD68-positive lung macrophage activities of a wild type (WT) and an FPR1 knockout model (FPR1KO) under normoxia conditions and under high-concentration oxygen administration conditions.

As a result, as illustrated in FIG. 5, it was confirmed that the activity of macrophages in lung tissues is significantly higher in the wild type hyperoxia control (WT-HC) than in the wild type normoxia control (WT-HC) ($P<0.05$).

Furthermore, it was confirmed that the activity of macrophages of the FPR1 knockout hyperoxia control is significantly lower than that of the wild type hyperoxia control (WT-HC) even though it is significantly higher than that of the wild type normoxia control (FPR1KO-HC) ($P<0.05$).

Further, an experiment for confirming the activity of myeloperoxidase (MPO) was performed using the experimental groups of Example 1-11.

Figure 6:
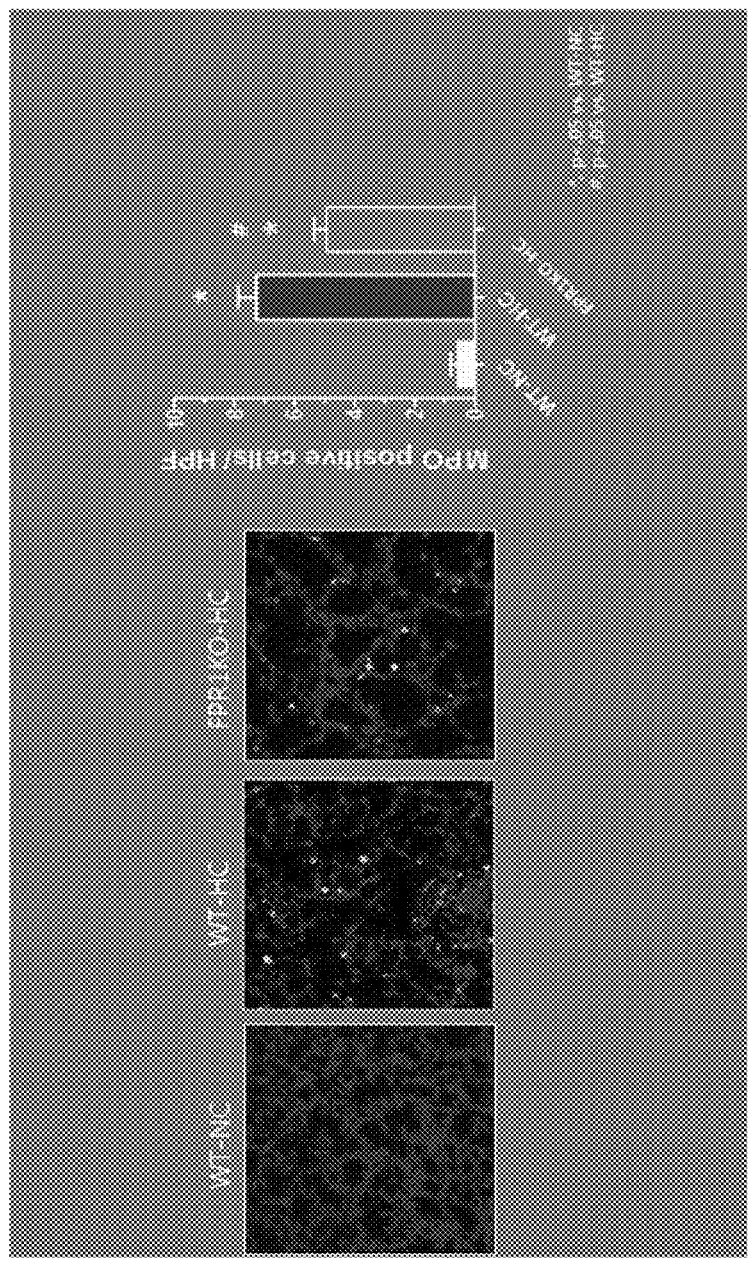
FIG. 6 illustrates the results of confirming the neutrophil MPO activities of a wild type (WT) and an FPR1 knockout model (FPR1KO) under normoxia conditions and under high-concentration oxygen administration conditions.

As a result, as illustrated in FIG. 6, it was confirmed that the MPO activity in lung tissues of the wild type hyperoxia control (WT-HC) is significantly higher than that of the wild type normoxia control (WT-NC) ($P<0.05$).

In addition, it was confirmed that the MPO activity of the FPR1 knockout hyperoxia control (FPR1KO-HC) is significantly lower than that of the wild type hyperoxia control (WT-HC) even though it is significantly higher than that of the wild type normoxia control (WT-NC) ($P<0.05$).

The above results indicate that in the case of an animal model in which the expression of FPR1 is reduced by knocking out FPR1, the inflammation of lung tissues associated with bronchopulmonary dysplasia is not increased compared to the wild type even though high-concentration oxygen is administered, and from this, it could be confirmed that FPR1 is involved in the onset of bronchopulmonary dysplasia.

2-5. Confirmation of Angiogenesis in Wild Type (WT) and FPR1 Knockout Model (FPR1KO)

An experiment for confirming angiogenesis in lung tissues was performed using the experimental groups of Example 1-11.

Figure 7:
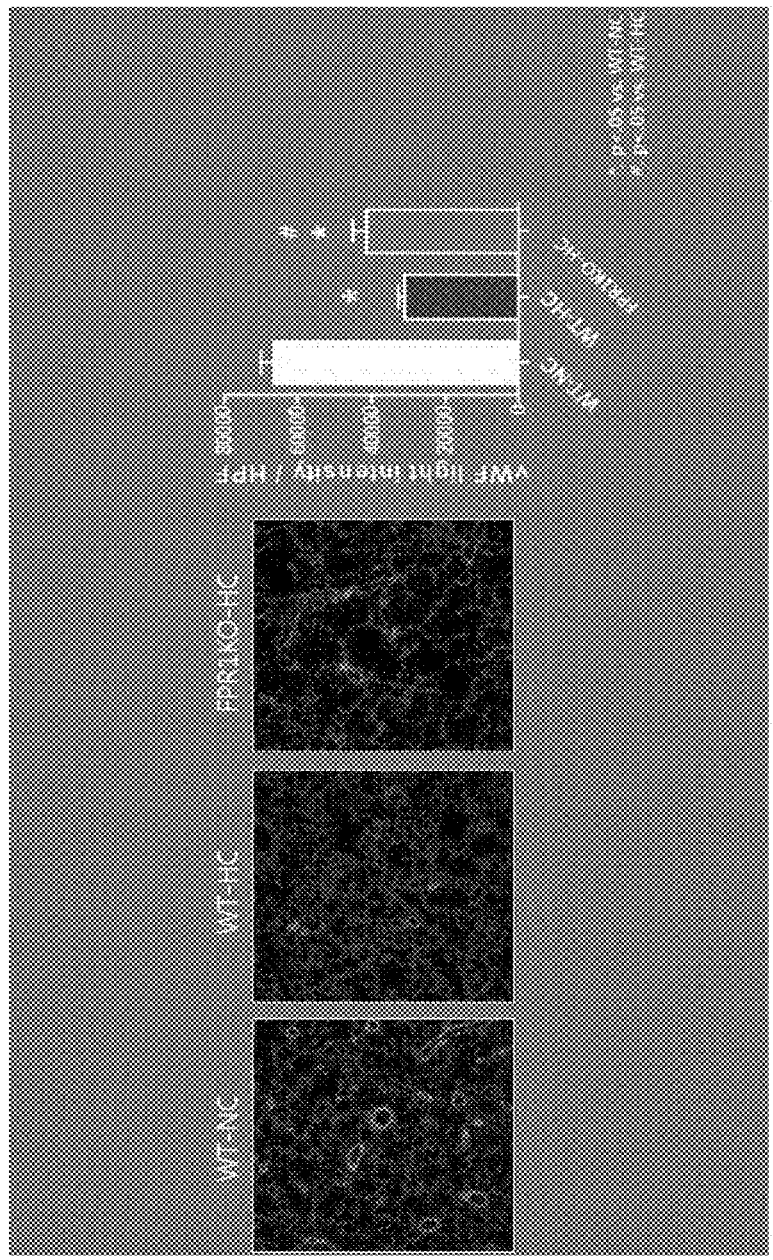
FIG. 7 illustrates the results of confirming the degree of angiogenesis of a wild type (WT) and an FPR1 knockout model (FPR1KO) under normoxia conditions and under high-concentration oxygen administration conditions.

As a result, as illustrated in FIG. 7, it was confirmed that the angiogenesis of lung tissues in the wild type hyperoxia control (WT-HC) is significantly smaller than in the wild type normoxia control (WT-NC) ($P<0.05$).

Furthermore, it was confirmed that even though the angiogenesis of the FPR1 knockout hyperoxia control (FPR1KO-HC) is significantly smaller than that of the wild type normoxia control (WT-NC), its angiogenesis in lung tissues is significantly larger than that of the wild type hyperoxia control (WT-HC) ($P<0.05$).

The above results confirm that when the expression of FPR1 is reduced by knocking out FPR1, pathological characteristics of bronchopulmonary dysplasia do not occur or weakly occur even though high-concentration oxygen is administered, and from this, it could be confirmed that FPR1 is involved in bronchopulmonary dysplasia.

Figure 8:
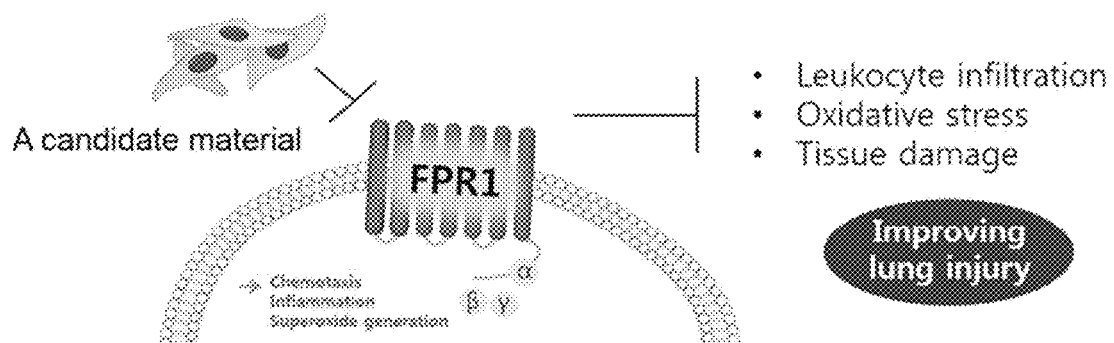
FIG. 8 illustrates a schematic view of the mechanism by which the candidate material of the present invention mitigates the bronchopulmonary dysplasia conditions by suppressing FPR1.
Figure 9:
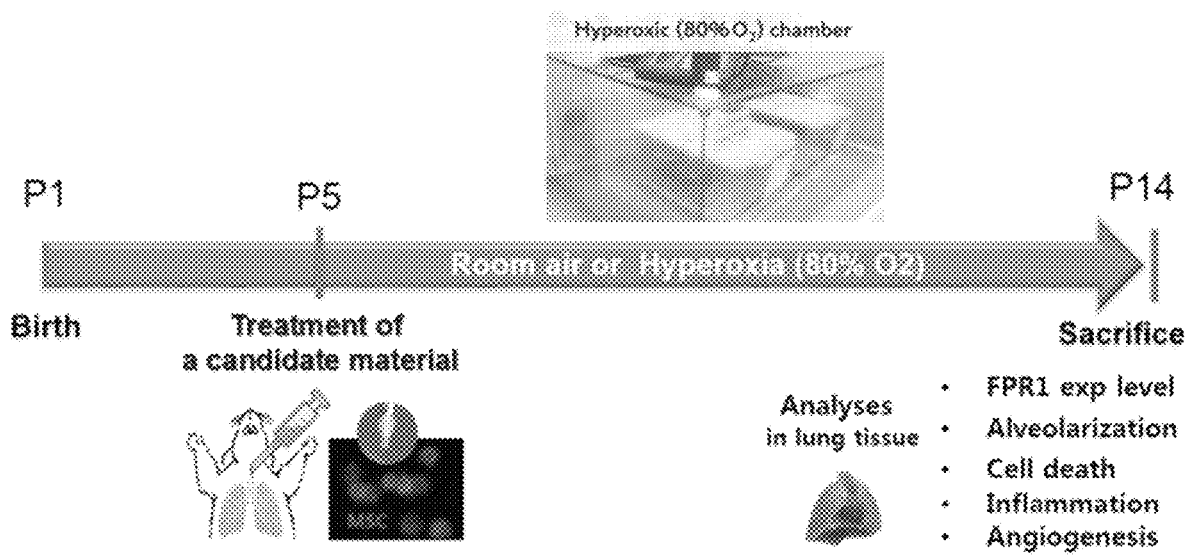
FIG. 9 illustrates a schematic view of the screening method according to the present invention.

Therefore, as illustrated in FIGS. 8 and 9, a material which reduces the expression or activity of the FPR1 gene can be screened as a material for preventing or treating bronchopulmonary dysplasia (BPD) by treating cells exhibiting bronchopulmonary dysplasia (BPD) conditions with a candidate material.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

According to the present invention, it is possible to find a therapeutic agent for bronchopulmonary dysplasia conveniently and rapidly by treating cells exhibiting bronchopulmonary dysplasia (BPD) conditions with a candidate material to screen a material which reduces the expression or activity level of FPR1 or the Fpr1 gene compared to a non-treatment group through measurement of the expression or activity of FPR1 or the Fpr1 gene in the cells.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A screening method for a material for preventing or treating bronchopulmonary dysplasia (BPD), the method comprising the following steps:
   (a) treating cells exhibiting bronchopulmonary dysplasia (BPD) conditions with a candidate material;
   (b) measuring the expression or activity of formyl peptide receptor 1 (FPR1) in the cells after treatment of the candidate material; and
   (c) selecting a material which reduces the expression or activity level of FPR1 compared to a non-treatment group as a material for preventing or treating bronchopulmonary dysplasia (BPD),
   wherein the FPR1 gene consists of a nucleic acid sequence represented by any one selected from the group consisting of SEQ ID NO: 1, SEQ ID NO: 2, and SEQ ID NO: 3, and
   wherein the FPR1 protein consists of an amino acid sequence represented by any one selected from the group consisting of SEQ ID NO: 4, SEQ ID NO: 5, and SEQ ID NO: 6.

2. The screening method of claim 1, wherein the candidate material is selected from the group consisting of compounds, microbial culture media or extracts, natural product extracts, nucleic acids and peptides.

3. The screening method of claim 1, wherein Step (b) is measured using one or more methods selected from the group consisting of immunoprecipitation, immunohistochemistry, microarray, northern blotting, western blotting, enzyme-linked immunosorbent assay (ELISA), polymerase chain reaction (PCR), and immunofluorescence.

* * * * *